United States Patent
Carbunaru et al.

(10) Patent No.: US 8,744,592 B2
(45) Date of Patent: *Jun. 3, 2014

(54) EFFICIENT EXTERNAL CHARGER FOR AN IMPLANTABLE MEDICAL DEVICE OPTIMIZED FOR FAST CHARGING AND CONSTRAINED BY AN IMPLANT POWER DISSIPATION LIMIT

(75) Inventors: Rafael Carbunaru, Valley Village, CA (US); Jordi Parramon, Valencia, CA (US); Robert Ozawa, Woodland Hills, CA (US); Jess Shi, Northridge, CA (US); Joey Chen, Valencia, CA (US); Md. Mizanur Rahman, Stevenson Ranch, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 720 days.

This patent is subject to a terminal disclaimer.

(21) Appl. No.: 12/575,733

(22) Filed: Oct. 8, 2009

(65) Prior Publication Data

US 2011/0087307 A1    Apr. 14, 2011

(51) Int. Cl.
- *A61N 1/00* (2006.01)
- *H02J 7/00* (2006.01)
- *A61N 1/378* (2006.01)
- *A61N 1/372* (2006.01)
- *A61N 1/36* (2006.01)

(52) U.S. Cl.
CPC ........... *A61N 1/3787* (2013.01); *A61N 1/37205* (2013.01); *A61N 1/3605* (2013.01); *A61N 1/37217* (2013.01)
USPC ............................... 607/61; 607/33; 320/108

(58) Field of Classification Search
USPC ............................ 607/32–33, 60–61; 320/108
See application file for complete search history.

(56) References Cited

U.S. PATENT DOCUMENTS 6,185,452 B1 * 2/2001 Schulman et al. .............. 604/20
7,200,504 B1    4/2007 Fister (Continued)

FOREIGN PATENT DOCUMENTS

WO    2008048321    4/2008

OTHER PUBLICATIONS

U.S. Appl. No. 12/471,626, filed May 26, 2009, Ozawa et al.

(Continued)

*Primary Examiner* — Christopher Koharski
*Assistant Examiner* — Catherine Voorhees
(74) *Attorney, Agent, or Firm* — Wong, Cabello, Lutsch, Rutherford & Brucculeri, LLP.

(57) ABSTRACT

An improved external charger for a battery in an implantable medical device (implant), and technique for charging the battery using such improved external charger, is disclosed. In one example, simulation data is used to model the power dissipation of the charging circuitry in the implant at varying levels of implant power. A power dissipation limit is chosen to constrain the charging circuitry from producing an inordinate amount of heat to the tissue surrounding the implant, and duty cycles are determined for the various levels of input intensities to ensure that the power limit is not exceeded. A maximum simulated average battery current determines the optimal (i.e., quickest) battery charging current, and at least an optimal value for a parameter indicative of that current, for example, the voltage across the battery charging circuitry, is determined and stored in the external charger. During charging, the actual value for that parameter is reported from the implant to the external charger, which in turn adjusts the intensity and/or duty cycle of the magnetic charging field consistent with the simulation to ensure that charging is as fast as possible, while still not exceeding the power dissipation limit.

16 Claims, 14 Drawing Sheets

(56) References Cited

U.S. PATENT DOCUMENTS

| | | |
|---|---|---|
| 7,209,792 B1 * | 4/2007 | Parramon et al. ............. 607/120 |
| 7,286,880 B2 | 10/2007 | Olson et al. |
| 2003/0078634 A1 | 4/2003 | Schulman et al. |
| 2007/0060980 A1 | 3/2007 | Strother et al. |
| 2009/0018618 A1 * | 1/2009 | Parramon et al. ............... 607/60 |
| 2009/0096413 A1 * | 4/2009 | Partovi et al. ................. 320/108 |
| 2009/0112291 A1 | 4/2009 | Wahlstrand et al. |
| 2010/0114216 A1 * | 5/2010 | Krause et al. ..................... 607/5 |
| 2010/0141042 A1 * | 6/2010 | Kesler et al. ................... 307/104 |
| 2010/0305663 A1 * | 12/2010 | Aghassian ....................... 607/61 |
| 2011/0046699 A1 * | 2/2011 | Mazanec ......................... 607/61 |
| 2011/0121777 A1 * | 5/2011 | Carbunaru et al. ........... 320/108 |

OTHER PUBLICATIONS

U.S. Appl. No. 12/562,694, filed Sep. 18, 2009, Aghassian.

\* cited by examiner

Vbat = 3.1V:

| P145 | P147 | P162 | P164 | P170 | Pfes | Ptotal |
|---|---|---|---|---|---|---|
| 4.734 mW | 6.655 mW | 1.029 mW | 0.531 mW | 0.047 mW | 0.322 mW | 8.583 mW |
| 17.290 | 11.792 | 1.609 | 2.198 | 0.618 | 0.503 | 16.719 |
| 30.495 | 18.663 | 2.149 | 4.224 | 1.819 | 0.672 | 27.527 |
| 44.200 | 24.971 | 2.686 | 6.567 | 3.522 | 0.839 | 38.585 |
| 58.344 | 33.063 | 3.236 | 9.280 | 5.671 | 1.011 | 52.261 |
| 65.536 | 37.518 | 3.510 | 10.779 | 6.839 | 1.097 | 59.743 |
| 68.925 | 40.335 | 3.726 | 11.426 | 8.873 | 1.164 | 65.525 |
| 72.107 | 43.771 | 4.027 | 12.131 | 12.365 | 1.258 | 73.553 |
| 75.002 | 47.588 | 4.385 | 12.911 | 17.020 | 1.370 | 83.274 |
| 77.767 | 51.877 | 4.806 | 13.637 | 22.801 | 1.502 | 94.623 |
| 87.835 | 72.376 | 6.927 | 16.606 | 53.026 | 2.165 | 151.100 |

Vbat = 3.1V:

| Duty Cycle = 32 mW/ Ptotal | Ibat(avg) = DC * Ibat |
|---|---|
| 90.0 % | 1.372 mA |
| 90.0 | 4.984 |
| 90.0 | 8.744 |
| 82.9 | 11.615 |
| 61.2 | 11.256 |
| 53.6 | 11.032 |
| 48.8 | 10.562 |
| 43.5 | 9.834 |
| 38.4 | 9.024 |
| 33.8 | 8.226 |
| 21.2 | 5.795 |

● ● ●
(Fig. 5B)

| Duty Cycle = 25.6 mW/ Ptotal | Ibat(avg) = DC * Ibat |
|---|---|
| 90.0 % | 1.372 mA |
| 90.0 | 4.984 |
| 90.0 | 8.744 |
| 66.3 | 9.292 |
| 49.0 | 9.004 |
| 42.9 | 8.825 |
| 39.1 | 8.449 |
| 34.8 | 7.867 |
| 30.7 | 7.219 |
| 27.1 | 6.581 |
| 16.9 | 4.636 |

*Figure 5C*

EFFICIENT EXTERNAL CHARGER FOR AN IMPLANTABLE MEDICAL DEVICE OPTIMIZED FOR FAST CHARGING AND CONSTRAINED BY AN IMPLANT POWER DISSIPATION LIMIT

FIELD OF THE INVENTION

The present invention relates generally to an external charger used to inductively charge a rechargeable battery within an implantable medical device such as a neurostimulator.

BACKGROUND

Implantable stimulation devices generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, occipital nerve stimulators to treat migraine headaches, and other neural stimulators to treat urinary incontinence, sleep apnea, shoulder sublaxation, etc. The present invention may find applicability in all such applications and in other implantable medical device systems, although the description that follows will generally focus on the use of the invention in a Bion™ microstimulator device system of the type disclosed in U.S. patent application Ser. No. 12/425,505, filed Apr. 17, 2009.

Microstimulator devices typically comprise a small generally-cylindrical housing which carries electrodes for producing a desired stimulation current. Devices of this type are implanted proximate to the target tissue to allow the stimulation current to stimulate the target tissue to provide therapy for a wide variety of conditions and disorders. A microstimulator usually includes or carries stimulating electrodes intended to contact the patient's tissue, but may also have electrodes coupled to the body of the device via a lead or leads. A microstimulator may have two or more electrodes. Microstimulators benefit from simplicity. Because of their small size, the microstimulator can be directly implanted at a site requiring patient therapy.

FIG. 1 illustrates an exemplary implantable microstimulator 100. As shown, the microstimulator 100 includes a power source 145 such as a battery, a programmable memory 146, electrical circuitry 144, and a coil 147. These components are housed within a capsule 202, which is usually a thin, elongated cylinder, but may also be any other shape as determined by the structure of the desired target tissue, the method of implantation, the size and location of the power source 145 and/or the number and arrangement of external electrodes 142. In some embodiments, the volume of the capsule 202 is substantially equal to or less than three cubic centimeters.

The battery 145 supplies power to the various components within the microstimulator 100, such the electrical circuitry 144 and the coil 147. The battery 145 also provides power for therapeutic stimulation current sourced or sunk from the electrodes 142. The power source 145 may be a primary battery, a rechargeable battery, a capacitor, or any other suitable power source. Systems and methods for charging a rechargeable battery 145 will be described further below.

The coil 147 is configured to receive and/or emit a magnetic field that is used to communicate with, or receive power from, one or more external devices that support the implanted microstimulator 100, examples of which will be described below. Such communication and/or power transfer may be transcutaneous as is well known.

The programmable memory 146 is used at least in part for storing one or more sets of data, including electrical stimulation parameters that are safe and efficacious for a particular medical condition and/or for a particular patient. Electrical stimulation parameters control various parameters of the stimulation current applied to a target tissue including, but not limited to, the frequency, pulse width, amplitude, burst pattern (e.g., burst on time and burst off time), duty cycle or burst repeat interval, ramp on time and ramp off time of the stimulation current, etc.

The illustrated microstimulator 100 includes electrodes 142-1 and 142-2 on the exterior of the capsule 202. The electrodes 142 may be disposed at either end of the capsule 202 as illustrated, or placed along the length of the capsule. There may also be more than two electrodes arranged in an array along the length of the capsule. One of the electrodes 142 may be designated as a stimulating electrode, with the other acting as an indifferent electrode (reference node) used to complete a stimulation circuit, producing monopolar stimulation. Or, one electrode may act as a cathode while the other acts as an anode, producing bipolar stimulation. Electrodes 142 may alternatively be located at the ends of short, flexible leads. The use of such leads permits, among other things, electrical stimulation to be directed to targeted tissue(s) a short distance from the surgical fixation of the bulk of the device 100.

The electrical circuitry 144 produces the electrical stimulation pulses that are delivered to the target nerve via the electrodes 142. The electrical circuitry 144 may include one or more microprocessors or microcontrollers configured to decode stimulation parameters from memory 146 and generate the corresponding stimulation pulses. The electrical circuitry 144 will generally also include other circuitry such as the current source circuitry, the transmission and receiver circuitry coupled to coil 147, electrode output capacitors, etc.

The external surfaces of the microstimulator 100 are preferably composed of biocompatible materials. For example, the capsule 202 may be made of glass, ceramic, metal, or any other material that provides a hermetic package that excludes water but permits passage of the magnetic fields used to transmit data and/or power. The electrodes 142 may be made of a noble or refractory metal or compound, such as platinum, iridium, tantalum, titanium, titanium nitride, niobium or alloys of any of these, to avoid corrosion or electrolysis which could damage the surrounding tissues and the device.

The microstimulator 100 may also include one or more infusion outlets 201, which facilitate the infusion of one or more drugs into the target tissue. Alternatively, catheters may be coupled to the infusion outlets 201 to deliver the drug therapy to target tissue some distance from the body of the microstimulator 100. If the microstimulator 100 is configured to provide a drug stimulation using infusion outlets 201, the microstimulator 100 may also include a pump 149 that is configured to store and dispense the one or more drugs.

Turning to FIG. 2, the microstimulator 100 is illustrated as implanted in a patient 150, and further shown are various external components that may be used to support the implanted microstimulator 100. An external controller 155 may be used to program and test the microstimulator 100 via communication link 156. Such link 156 is generally a two-way link, such that the microstimulator 100 can report its status or various other parameters to the external controller 155. Communication on link 156 occurs via magnetic inductive coupling. Thus, when data is to be sent from the external controller 155 to the microstimulator 100, a coil 158 in the external controller 155 is excited to produce a magnetic field that comprises the link 156, which magnetic field is detected at the coil 147 in the microstimulator. Likewise, when data is to be sent from the microstimulator 100 to the external controller 155, the coil 147 is excited to produce a magnetic field that comprises the link 156, which magnetic field is detected at the coil 158 in the external controller. Typically, the magnetic field is modulated, for example with Frequency Shift Keying (FSK) modulation or the like, to encode the data.

An external charger 151 provides power used to recharge the battery 145 (FIG. 1). Such power transfer occurs by energizing the coil 157 in the external charger 151, which produces a magnetic field comprising link 152. This magnetic field 152 energizes the coil 147 through the patient 150's tissue, and which is rectified, filtered, and used to recharge the battery 145 as explained further below. Link 152, like link 156, can be bidirectional to allow the microstimulator 100 to report status information back to the external charger 151. For example, once the circuitry 144 in the microstimulator 100 detects that the power source 145 is fully charged, the coil 147 can signal that fact back to the external charger 151 so that charging can cease. Charging can occur at convenient intervals for the patient 150, such as every night.

FIG. 3 illustrates salient portions of the microstimulator's power circuitry 160. Charging energy (i.e., the magnetic charging field) is received at coil 147 via link 152. The coil 147 in combination with capacitor 162 comprises a resonant circuit, or tank circuit, which produces an AC voltage at Va. This AC voltage is rectified by rectifier circuitry 164, which can comprise a well-known 4-diode bridge circuit, although it is shown in FIG. 3 as a single diode for simplicity. Capacitor 166 assists to filter the signal at node Vb, such that Vb is essentially a DC voltage, although perhaps having a negligible ripple. Intervening between Vb and the rechargeable battery 145 is charging circuitry 170, which ultimately takes the DC voltage Vb and uses it to produce a controlled battery charging current, Ibat. Charging circuitry 170 is well known. One skilled in the art will recognize that the power circuitry 160 may include other components not shown for simplicity.

It is generally desirable to charge the battery 145 as quickly as possible to minimize inconvenience to the patient. One way to decrease charging time is to increase the strength of the magnetic charging field by increasing the excitation current in the coil 157 of the external charger. Increasing the charging field will increase the current/voltage induced in the coil 147 of the microstimulator 100, which increases the battery charging current, Ibat. However, the strength of the magnetic charging field can only be increased so far before implant heating becomes a concern. One skilled in the art will understand that implant heating is an inevitable side effect of charging using magnetic fields. Heating can result from several different sources, such as eddy currents in conductive portions of the implant, or heating of the various components in the power circuitry 160. Implant heating is a serious safety concern; if an implant exceeds a given safe temperature (e.g., 41° C.), the tissue surrounding the implant may be aggravated or damaged.

The art has recognized that heating can be controlled by controlling the intensity of the magnetic charging field produced at the external charger 151. For example, the current flowing through charging coil 157 can be reduced to reduce the temperature of the implant during charging. The art has also recognized that heating can be regulated by duty cycling the charging field, i.e., by turning the charging field at the external charger 151 on and off. FIG. 4 generally shows the temperature of the implant, T(IPG), for two different duty cycles, DC1 and DC2, for a given magnetic charging field. The first duty cycle, DC1, equals 50%, because the magnetic charging field is on for 50% of the time (i.e., t1(on)=t1(off)). The second duty cycle, DC2, equals 75%, and hence the magnetic charger field stays on that much longer (i.e., t2(on)= 3t2(off)). As one would expect, higher duty cycles result in higher temperatures in the implant: i.e., T1(IPG)<T2(IPG) as shown.

While changing the intensity or duty cycling of the magnetic charging field produced by the external charger 151 can be an effective means of controlling implant temperature, the inventors have realized that such approaches do not adequately address important issues. First, known prior approaches do not address whether the magnetic charging field intensity, duty cycle, or both, should be modified as a means of temperature control. Moreover, such prior techniques are not understood to consider efficient charging of the implant battery 145. Thus, one can change the intensity and/or duty cycle of the magnetic charging field to arrive at suitable temperature control, but the particular parameters chosen may provide a charging power to the battery that is unnecessarily low, which would prolong charging. Prolonged charging is inefficient, because that patient must wait an inordinate amount of time to fully charge the battery 145 in his or her implant. Understandably, patients do not desire charging to take any longer than necessary.

Finding optimal charging conditions (intensity, duty cycle) thus remains unknown with such prior art techniques, and this disclosure presents a technique to combat this problem, and to make charging more efficient from both a time and implant heating perspective.

BRIEF DESCRIPTION OF THE DRAWINGS

FIGS. 5A-5C illustrate a simulation in accordance with one example of the disclosed technique.

DETAILED DESCRIPTION

An improved external charger for a battery in an implantable medical device (implant), and technique for charging the battery using such improved external charger, is disclosed. In one example, simulation data is used to model the power dissipation of the charging circuitry in the implant at varying levels of implant power. A power dissipation limit is chosen to constrain the charging circuitry from producing an inordinate amount of heat to the tissue surrounding the implant, and duty cycles are determined for the various levels of input intensities to ensure that the power limit is not exceeded. A maximum simulated average battery current determines the optimal (i.e., quickest) battery charging current, and at least an optimal value for a parameter indicative of that current, for example, the voltage across the battery charging circuitry, is determined and stored in the external charger. During charging, the actual value for that parameter is reported from the implant to the external charger, which in turn adjusts the intensity and/or duty cycle of the magnetic charging field consistent with the simulation to ensure that charging is as fast as possible, while still not exceeding the power dissipation limit. As a result, charging is optimized to be as fast as possible, while still safe from a tissue heating perspective.

Figure 1:
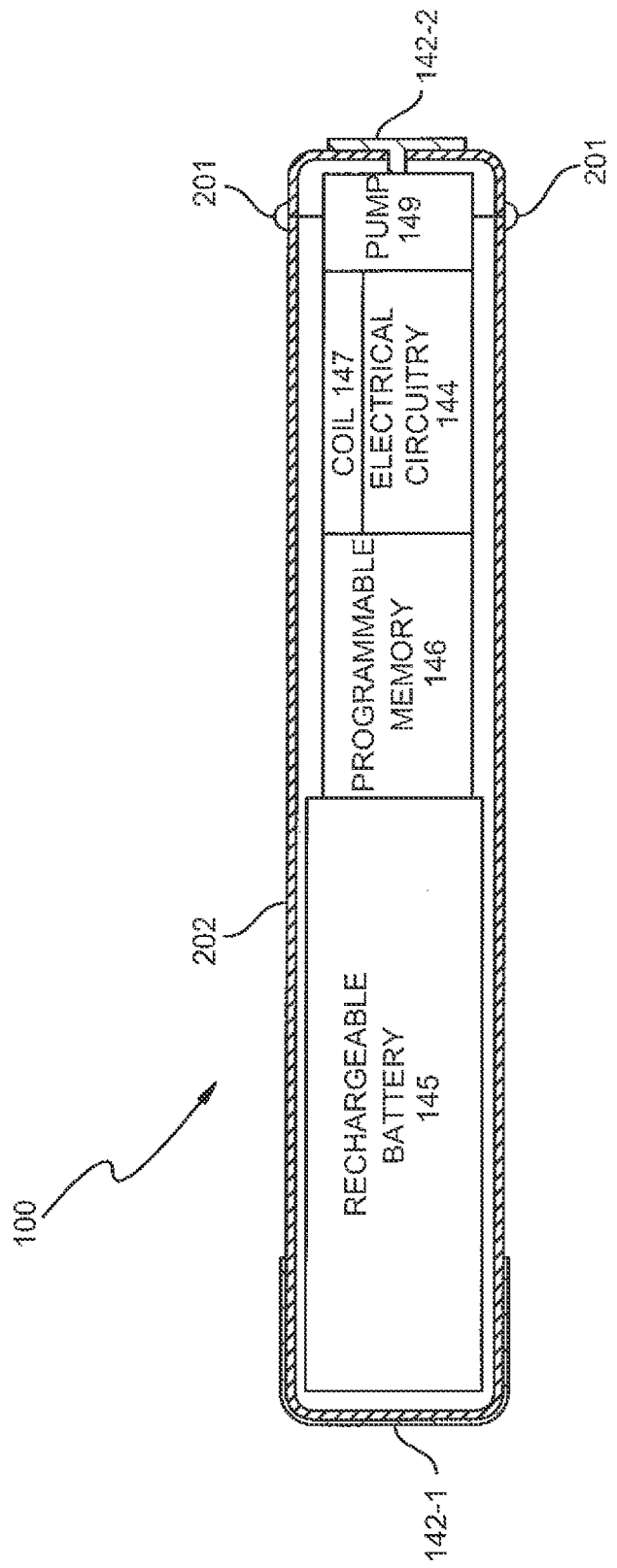
FIG. 1 illustrates a microstimulator implant, including a battery requiring periodical recharging from an external charger, in accordance with the prior art.
Figure 2:
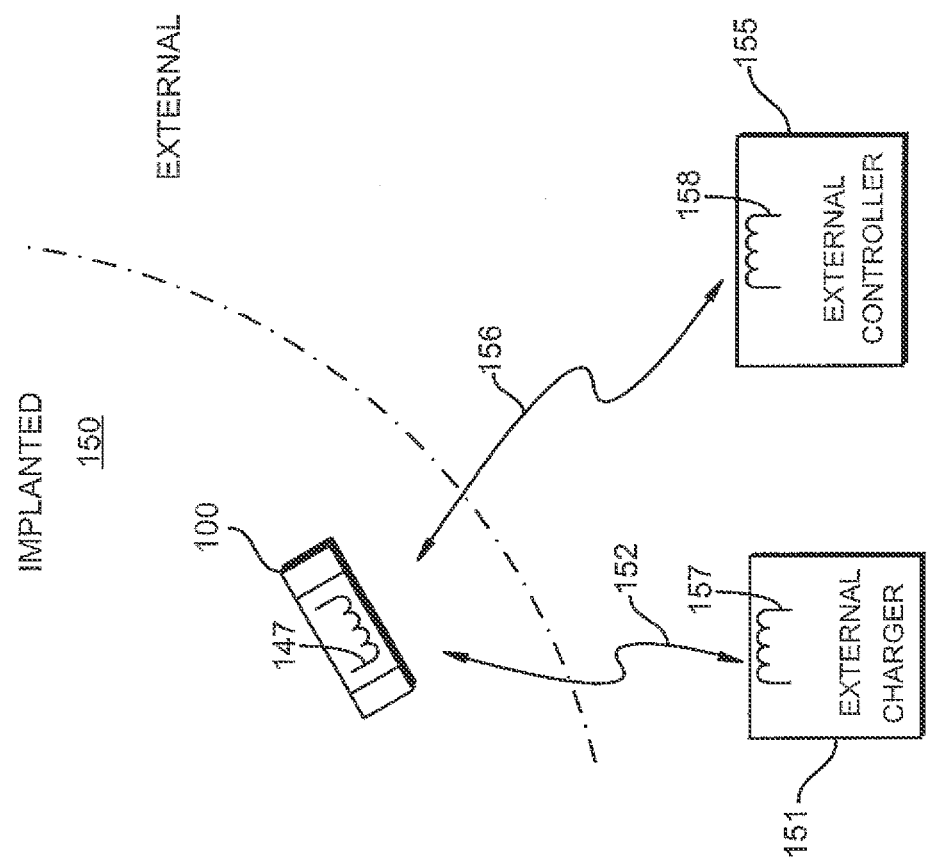
FIG. 2 shows the implant in communication with, inter alia, an external charger in accordance with the prior art.
Figure 3:
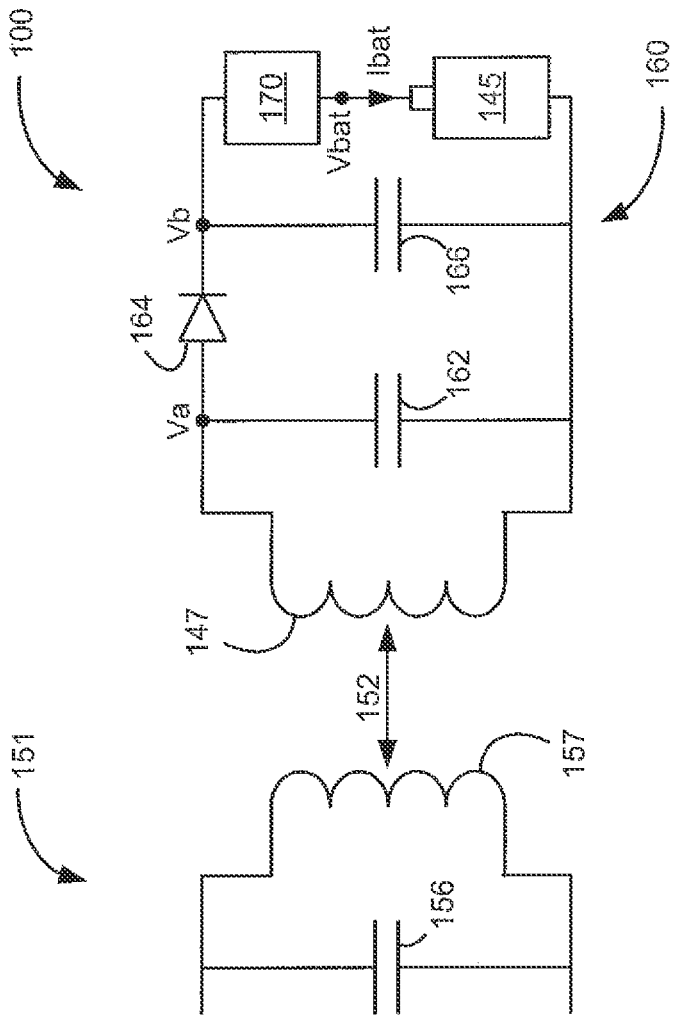
FIG. 3 illustrates charging circuitry within the implant in accordance with the prior art.
Figure 4:
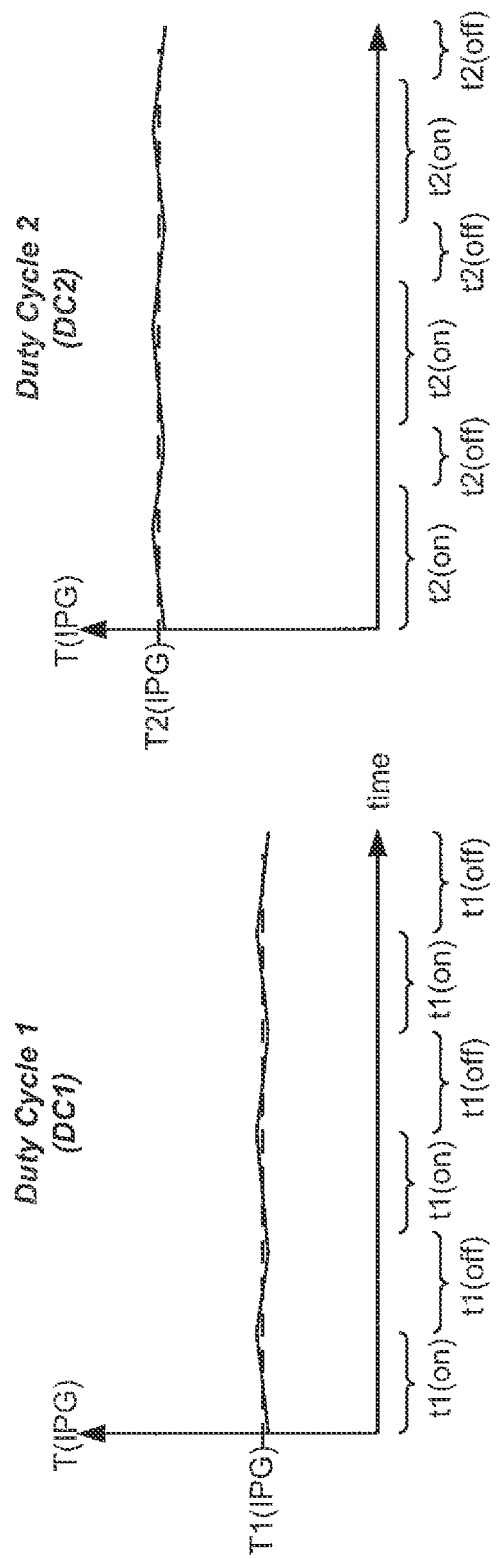
FIG. 4 illustrates duty cycling the power at the external charger to control implant temperature in accordance with the prior art.

Prior to discussing the disclosed technique, reference is made to the microstimulator power circuitry 160 of FIG. 3. While this circuitry is used in an explanation of the technique, it should be understood that the disclosed technique is not limited to use with the particular power circuitry shown 160.

Various components in the power circuitry 160 within the implant will draw power during the reception of a magnetic charging field from the external charger 151. In particular, the coil 147, its associated tank capacitor 162, the rectification circuitry (diode) 164, charging circuitry 170, and the battery 145 itself will all dissipate power in the form of heat. (Capacitor 166 will draw a comparatively negligible amount of power, and thus is not further discussed). The sum total of the powers dissipated by each of these components must be considered when understanding how the tissue surrounding the implant 100 will heat up during a charging session. For example, animal studies show that for a particular multiple-electrode microstimulator device, a radiated power of 32 mW will raise the temperature of the tissue surrounding the implant by approximately 4° C., while a total radiated power of 25.6 mW will raise the temperature by 3.2° C. Of course, these values are only exemplary, and could vary; future values could be determined that are more accurate, safer, etc. In any event, such animal studies have correlated power dissipation to tissue heating for a given implant.

An aspect of the disclosed technique seeks to keep the total dissipated power at or below a limit to ensure that the patient's tissue will not overheat. Because a 4° C. rise in tissue temperature is generally accepted as safe for a patient, one example of the technique labors to keep the total power dissipated from the power circuitry 160 at or below 32 mW. Of course, different limits could be chosen, such as the 25.6 mW/3.2° C. limit discussed above.

Figure 5A:
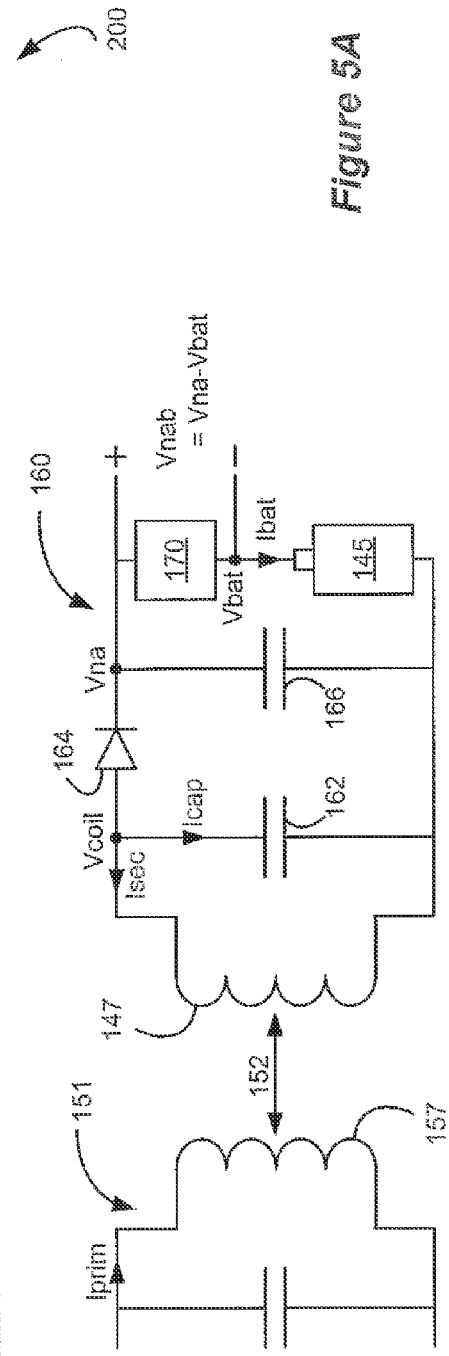
Figure 5B:
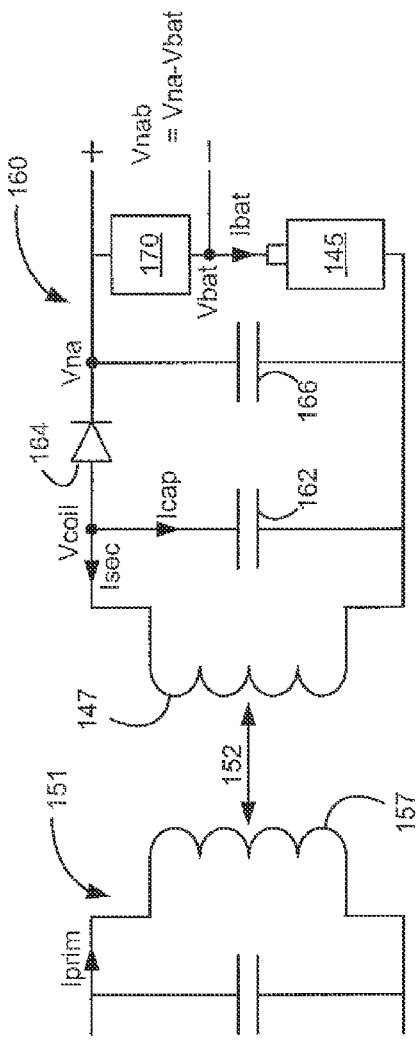

The inventors have noticed through simulations that power dissipation from the various components in the power circuitry 160 is complex and non-linear in nature. One such simulation 200 is illustrated in FIGS. 5A, 5B, and 5C. As will be discussed further below, certain portions from simulation 200 are stored in the external charger 151 and will be used to regulate charging. However, before discussing a charging operation, simulation 200 is explained.

Simulation 200 shows the effect of varying the intensity (e.g., current) in the external controller's charging coil 157 (Iprim(rms)) on the various components in the power circuitry 160 of the implant 100, with each successive row representing an increasing value for Iprim(rms). Because the simulation 200 results will vary depending on how full or depleted the implant battery 145 is at a given moment, the depicted simulation assumes a battery with a particular voltage of Vbat=3.1 V. Although not depicted, other simulations 200 at other battery voltages (e.g., 3.3V, 3.7V, 4.1V, etc.) may also be generated to provide accurate simulation results as battery capacity starts to fill during charging. For example, if the battery 145 has a full capacity of Vbat=4.1V, then simulations 200 may be generated for Vbat=3.1 V, 3.3V, 3.7V, and 4.1V to cover a range of expected battery capacity. However, if the various parameters within simulation 200 do not vary appreciably with Vbat, then the generation of additional simulations 200 for different battery capacities may not be necessary. A simulation program useful in generating a simulation 200 is Mentor Graphics Design Architect.

The simulation 200 assumes a particular coupling factor between the primary coil 157 in the external charger 151 and the secondary coil 147 in the implant 100, which coupling factor is modeled taking into account factors affecting such coupling, such as coil inductances, coil alignment, the distance and permittivity of any materials (e.g., tissue, air) between the coils, etc. In the depicted simulation, a coupling factor k=0.017 was chosen to conservatively simulate a worst case alignment between the charging coils 157 and 147. In any event, the coupling factor ultimately results in a simulated induced current in charging coil 147 in the implant (Isec (rms)), a current in the associated tank capacitor 162 (Icap (rms)), a voltage across the coil 147 (Vcoil(rms)), a DC voltage produced by the rectifier circuit (diode) 164 (Vna), a battery charging current (Ibat), a battery voltage (Vbat) resulting from the input of the battery charging current, which battery voltage takes into account the internal resistance of the battery 145. Of course, relevant parameters for the various components in the power circuitry 160 (resistances, capacitance, inductances, coupling factor, etc.) are input into the simulation program to allow it to generate the simulation results.

Figure 6:
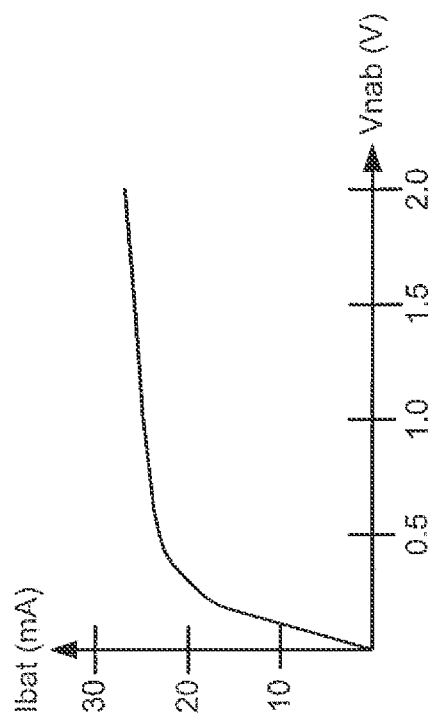
FIG. 6 illustrates the relation between battery charging current (Ibat) and the voltage across the battery protection circuitry (Vnab) as revealed from the simulation of FIG. 5.

Of particular interest in simulation 200 is the voltage across the charging circuitry 170, Vnab, which represents the difference between Vna and Vbat. Because the charging circuitry 170 is in line with the battery charging current, Ibat, any voltage build up across the charging circuitry comprises undesired heat generation. Unfortunately, modeling shows that the amount of heat dissipation from the charging circuitry 170 increases essentially exponentially as the battery charging current increases. This is shown in FIG. 6: as the battery charging current Ibat increases, the voltage built up across the battery protection circuitry Vnab increases at an increasingly fast rate. Because the power dissipated by the charging circuit 170 equals the current times the voltage, the power too essentially exponentially increases. In short, the parameter Vnab represents charging power wasted as heat, and as will be seen below, is monitored and controlled in the disclosed technique to permit charging at an optimally efficient level.

From the various simulated voltages and currents in FIG. 5A, the simulation 200 can further calculate the power dissipated by the various components in the power circuitry 160, as shown in FIG. 5B, which powers essentially comprise the product of the voltage across and current through the various components. As shown, the power drawn by each component is represented by the element numeral for the component: for example, the power drawn by the battery 145 during charging is denoted as P145. Pfes represents power drawn by front end switches in series with the charging circuitry 170, which switches are not depicted for simplicity because their power dissipation are relatively small. The sum of the power dissipated by each of the components in the power circuitry 160 is shown in the last column in FIG. 5B (Ptotal).

A review of the Ptotal parameter in simulation 200 illustrates a tissue heating concern for the designer. As discussed earlier, an acceptable level of total power dissipated by the power circuitry 160 should not exceed the 32 mW power dissipation limit in one example—a temperature known by experimentation to increase surrounding tissue by 4° C. However, all but the top three rows in FIG. 5B exceed this value (bolded for easy viewing). In other words, simulation 200 shows that at higher external charger intensities (i.e., higher Iprim(rms)), the total heat generated in the implant 100 may be excessive.

One solution to keep the total power at or below 32 mW is to duty cycle the power at the external charger 151, which computed duty cycle is shown in FIG. 5C. The duty cycle insures that the power dissipation limit is not exceeded by dividing the limit (e.g., 32 mW) by the simulated total power draw assuming no duty cycling (Ptotal).

Figure 7:
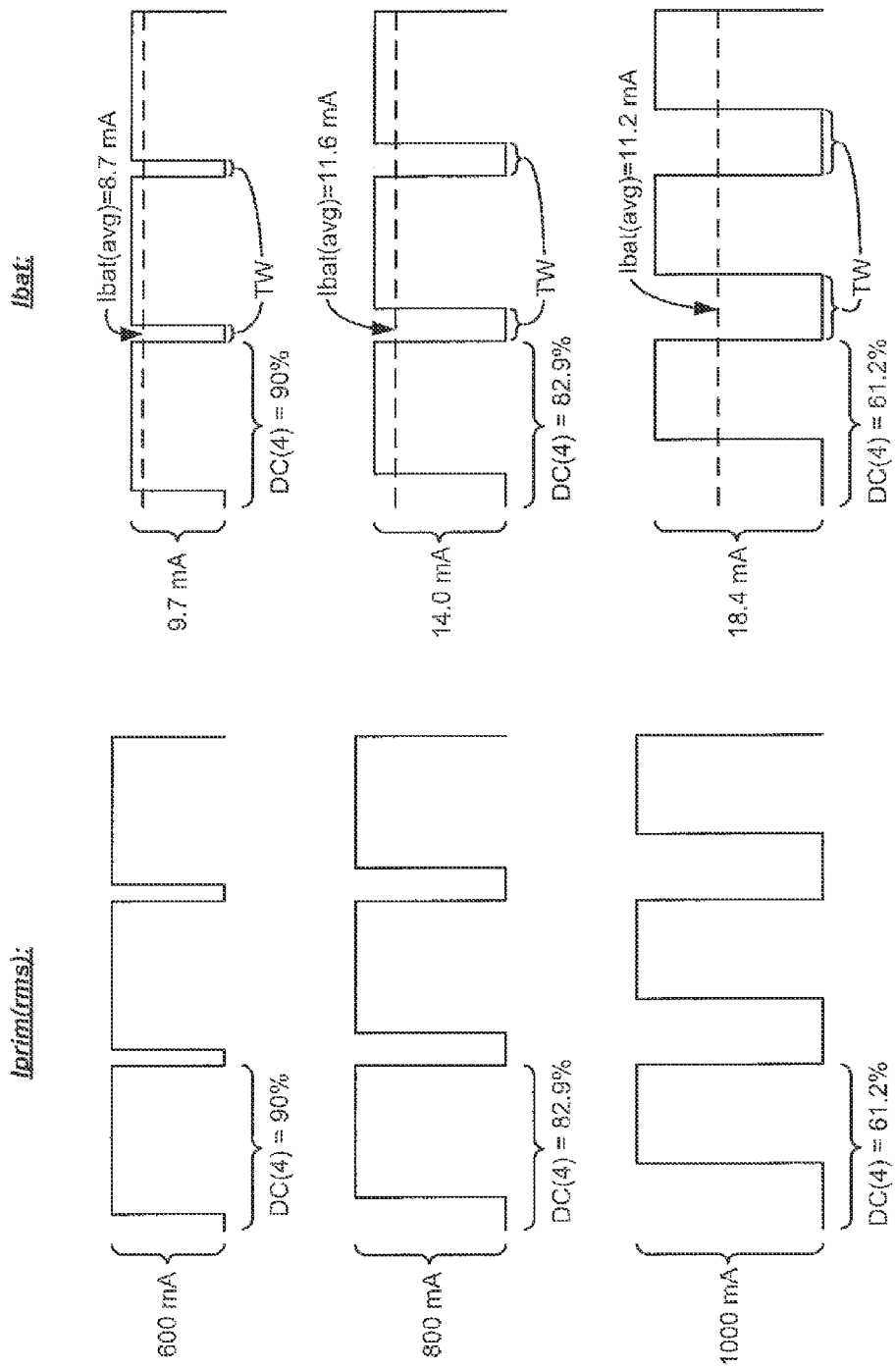
FIG. 7 illustrates various duty cycles determined for the simulation of FIG. 5 which will not exceed a prescribed power limit, and shows the application of such duty cycles on the power at the external charging coil (Iprim(rms)) and in the battery charging current (Ibat).

The results of such duty cycling are shown in FIG. 7 for the third, fourth, and fifth rows in the simulation 200, i.e., when Iprim(rms) equals 600, 800, and 1000 mA. In the third row, the simulated total power dissipated was 27.5 mW, which is below the 32 mW limit. Hence, duty cycling would not be required for this level of input power (i.e., for Iprim(rms)=600 mA). However, a duty cycle of 90% is imposed anyway to allow an off time, or telemetry window (TW), during which the implant 100 can back-telemeter data to the external charger 151. The telemetry window (TW) may be 10 sec for example, meaning that the period for duty cycling is typically about 10 times larger, or 100 sec. While the telemetry window TW can be fixed, it can also be made to vary depending on how long is needed to send data back to the external charger 151. For example, the TW can be set to the exact time needed for data transmission, with the on portion of the cycle similarly scaled to match the duty cycle required. A shorter duration for the total period of the duty cycle reduces ripple in the temperature of the implant 100.

As will be seen further below, it is advantageous to telemeter data (e.g., Vnab, Vbat) back to the external charger 151 to allow charging to be iteratively optimized in real time. As can be seen in FIG. 7, this duty cycle is imposed on the primary coil in the external charger (Iprim(rms)), which causes the same duty cycle in the battery charging current, Ibat. An average battery current, Ibat(avg), can be calculated from the product of Ibat and the duty cycle to give an over-time indication of the amount of charging current that is being received by the battery, despite the duty cycling. The significance of Ibat(avg) will be discussed further below.

In the fourth row of the simulation 200 (Iprim(rms)=800 mA), the simulated total power dissipated was 38.6 mW, above the 32 mW limit. Therefore, duty cycling is imposed as a heat control measure, in addition to the desire for an off period to allow for back telemetry. Such duty cycling equals 82.9% (32/38.6) to ensure a total dissipated power of not more than 32 mW. The fifth row is similarly processed to determine a duty cycle of 61.2%, and its effects on Iprim(rms) and Ibat are shown.

Additionally shown to the right in FIG. 5C are the computed duty cycles for the less-heat-intensive 25.6 mW/3.2° C. limit, which limit may be chosen to even further minimize patient discomfort or injury due to heat generation in the power circuitry 160. Again, the duty cycles are computed by dividing the limit (25.6 mW) by the simulated total powers (Ptotal).

Note from FIG. 7 that the average battery current, Ibat (avg), is maximized when Iprim equals 800 mA. This average maximum, Ibat(avg)(opt)=11.6 mA, represents the optimal charging current for the implant battery 145: it is the largest average current and hence will charge the implant battery the fastest. Moreover, because of the duty cycling leading to the calculation of the Ibat(avg) values, Ibat(avg)(opt) is at the same time optimized to allow no more than 32 mW power dissipation on average. Ibat(avg)(opt) is thus optimized for both speed and heat dissipation.

Figure 8:
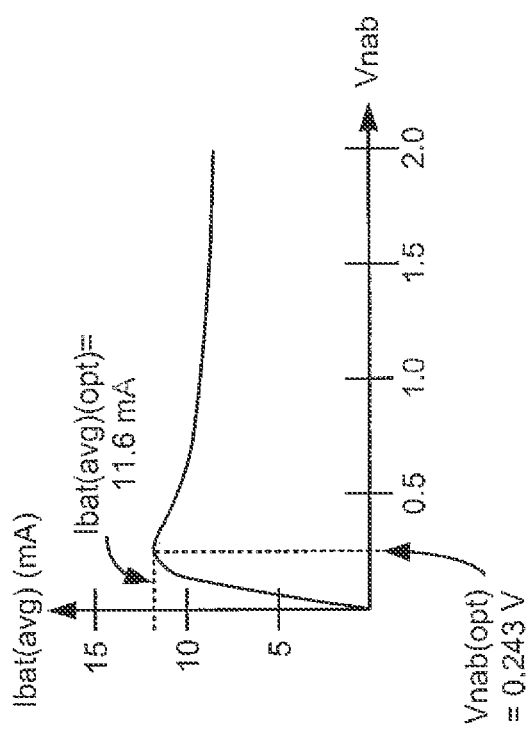
FIG. 8 illustrates the relation between the average battery charging current (Ibat(avg)) and Vnab as revealed from the simulation of FIG. 5, and shows the Vnab(opt) at which Ibat(avg) is maximized.

The disclosed technique seeks to maintain charging at this optimal average battery current. To so maintain Ibat(avg) (opt) during charging, it is useful to monitor a parameter indicative of the battery charging current, Ibat. One convenient parameter comprises Vnab, i.e., the voltage that builds across the charging circuitry 170, although other parameters indicative of the battery charging current could also be used (e.g., Vna). The Vnab parameter is easily measured in the implant, and as noted earlier represents wasted heat. FIG. 8 shows a graph of Ibat(avg) v. Vnab for the simulation 200 for the 32 mW/4° C. limit, and shows the maximum at 11.6 mA. The corresponding Vnab for this value, Vnab(opt) is 0.243 V (see fourth row, FIG. 5A). Vnab(opt) thus represents the voltage across the charging circuitry 170 that provides the quickest charging of the implant battery 145, but which is safe from a heating perspective. As will be seen below, one implementation of the disclosed technique is to maintain Vnab at Vnab(opt) during charging.

Figure 9:
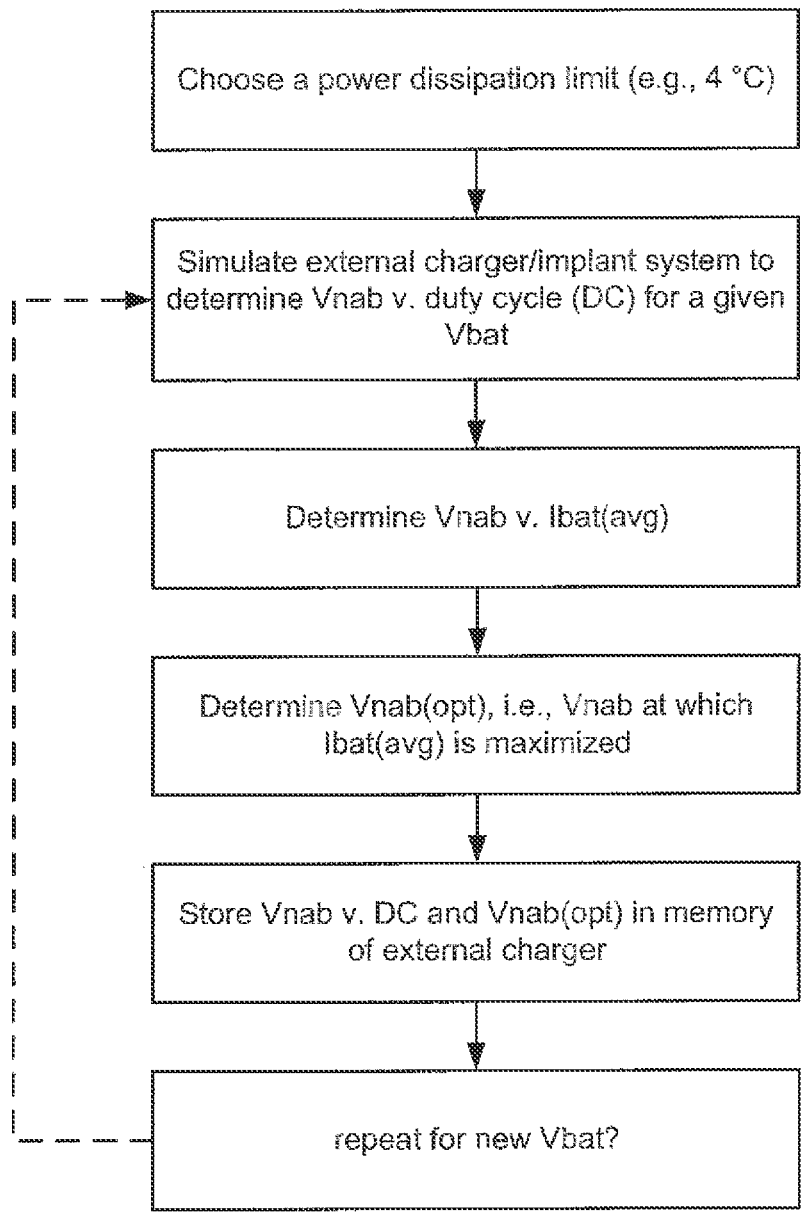
FIG. 9 illustrates storage of salient portions of the simulation to prepare the external charger for operation during an actual charging session, in accordance with one embodiment of the disclosed technique.

Prior to discussing use of the technique in an actual charging session, steps to this point in the process are summarized in FIG. 9, which steps lead to storing relevant parameters in the external charger 151. First, a power dissipation limit is chosen, such as the 32 mW/4° C. limit discussed previously. Then, the external charger 151/implant 100 system is simulated to determine the relationship between Vnab and the duty cycle needed to stay compliant with the power dissipation limit. This simulation can occur assuming a particular battery voltage (Vbat) for the battery 145 in the implant 100. Next, the relationship between Vnab and Ibat(avg) is determined using the duty cycle, and an optimal Vnab(opt) is determined which corresponds to the maximum Ibat(avg). Thereafter, Vnab v. DC, and Vnab(opt) are stored in memory of the external charger, as will be discussed further shortly. Thereafter, the preparation process repeats for a new battery voltage if necessary, but as noted earlier this may not be required if the various simulated parameters do not vary strongly with Vbat.

Figure 10:
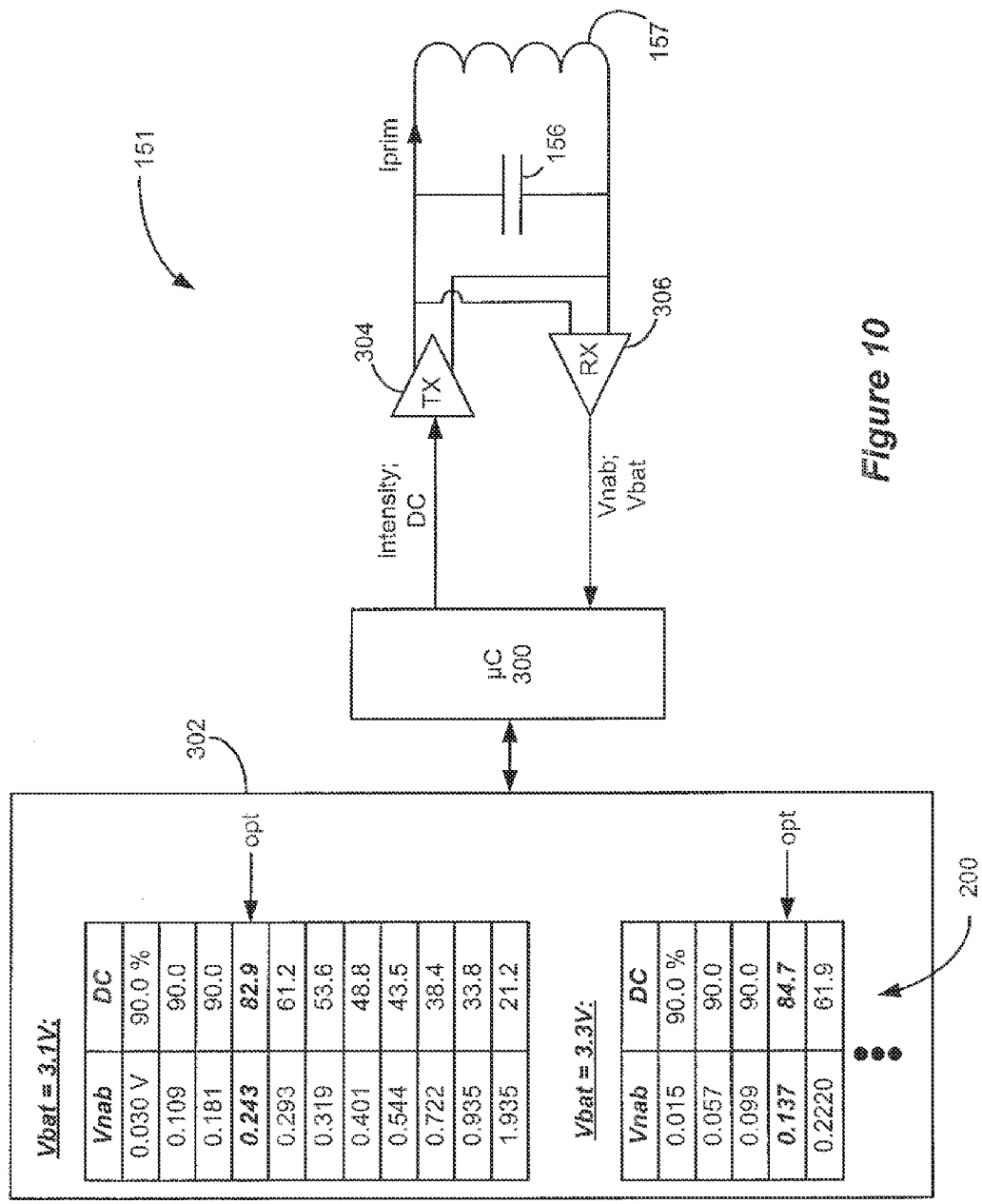
FIG. 10 illustrates circuitry in the external charger in accordance with one embodiment of the disclosed technique, including a memory storing salient portions of the simulation relevant to optimization of the charger's power parameters.

FIG. 10 shows the external charger 151 as prepared with the parameters stored from FIG. 9. Shown with particularity is a memory 302, which contains at least a portion of the simulation 200, including the Vnab v. DC relationship for the 32 mW power dissipation limit and Vnab(opt) for Vbat=3.1V. Also shown in part is the same information for Vbat=3.3V, although as just discussed this is not strictly necessary. Alternatively, memory 302 could contain the same information for other power dissipation limits (e.g., 25.6 mW/3.2° C.) as well, but this is not shown for simplicity. The memory 302 containing these parameters is coupled to (or could comprise part of) the microcontroller 300 in the external charger 151.

Also shown in FIG. 10 are the transmitter 304 and receiver 306 circuits coupled to the external charger's coil 157, which circuitry is well known. The transmitter 304 produces an AC signal to cause the L-C tank circuit (156/157) to resonate and in turn generate the magnetic charging field. As shown, the transmitter 304 receives control signals from the microcontroller 300 to indicate the intensity (e.g., the magnitude of Iprim) and the duty cycle of the transmitter 304. The receiver 306 receives data transmitted periodically from the implant 100, e.g., during the telemetry window (TW) or off portions of the duty cycle (see FIG. 7). Such data may be transmitted using radio-frequency (RF) telemetry, or Load Shift Keying (LSK) for example. (LSK is further discussed in U.S. patent application Ser. No. 12/354,406, filed Jan. 15, 2009, for example).

Traditionally, such back telemetry from the implant to the external charger is used to transmit the capacity of the battery 145 during charging (Vbat), which informs the external charger 151 when the battery is full and that charging can cease. Battery capacity is similarly reported in disclosed system, but additionally, the Vnab value measured at the implant 100 is also transmitted. Reporting of Vnab to the external charger 151 can take place at any suitable interval during charging, such as once every 100 seconds or so. The more frequently Vnab is reported, the more frequently charging can be optimized during the charging session.

Figure 11:
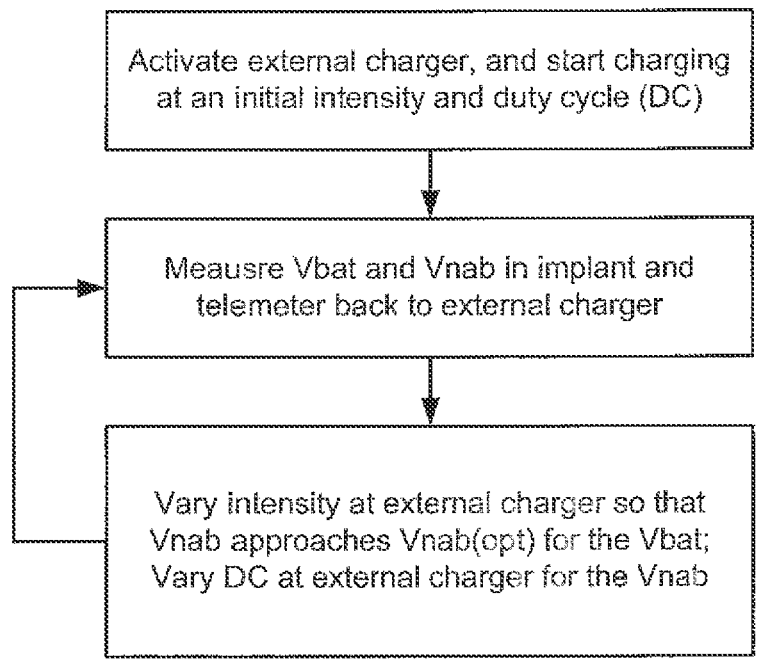
FIG. 11 illustrates a process in accordance with the disclosed technique for adjusting the power level and/or duty cycle of the power at the external charger in accordance with the stored simulation parameters.

With the basic structure of the external charger 151 understood, attention can now focus on how charger 151 operates during an actual charging session, which basic steps are shown in FIG. 11. First, the external charger 151 is turned on (e.g., by the patient), and generates a magnetic charging field using an initial intensity level (i.e., an initial Iprim) and an initial duty cycle. Simulation 200 does not help much in determining initial values for the power and duty cycle levels used at the external charger, as the coupling to the implant 100 during a real charging session cannot be perfectly known in advance. For example, different patients may have their implants located at different depths in their tissues, or may have different physical alignments between their external chargers and their implants. In any event, the initial power and duty cycle values are not important as they will be changed in accordance with the disclosed technique as charging progresses, although they are logically set to initial values guaranteed not to injure the patient.

Periodically during charging, for example, perhaps every 100 seconds, the battery voltage (Vbat) and the voltage across the charging circuitry (Vnab) are measured at the implant 100, and telemetered to the external charger. Again, such telemetry can comprise RF or LSK telemetry performed during the telemetry window (TW) or off periods in the duty cycle. How often to communicate, just like the time used for communication during the telemetry window (TW), may also be determined by the length of the needed communication between implant and charger. Increasing the frequency of communication will reduce temperature ripple in the implant 100.

Once Vnab is reported, the microcontroller 300 consults memory 302 to see if Vnab is optimal, i.e., if Vnab=Vnab(opt) for the reported Vbat. If not, intensity of the magnetic charging field is changed. For example, and referring to memory 300 in FIG. 10, if Vnab is near 0.293V for Vbat=3.1V, the microcontroller 300 would understand that the intensity is too high, and would reduce Iprim in an attempt to make Vnab approach Vnab(opt). Conversely, if Vnab is near 0.181V, Iprim would be increased.

At the same time, the duty cycle of the magnetic charging field would also be changed to match the Vnab being reported. Modifying the duty cycle to match Vnab is important to ensure proper compliance with the power dissipation limit. For example, and referring again to FIG. 10, assume again that Vnab is near 0.293V, but that the duty cycle currently imposed at the transmitter 304 is 85%. Reference to the stored parameters in memory 302 shows that this duty cycle is too high, and will produce too much heat, i.e., more than the 32 mW power dissipation limit. To keep the total dissipated power compliant with the limit, the microcontroller 300, upon consulting memory 302, will change the duty cycle to 61.2%.

As shown in FIG. 11, once such intensity and duty cycle adjustments are made at the external charger 151, the process repeats: Vbat and Vnab are again reported after some time, and the intensity and duty cycle adjusted again if necessary. It should be noted that such iterative adjustment of the power produced by the external charger 151 is particularly helpful in applications where the coupling between the external charger 151 and the implant 100 might change. For example, the patient may move the external charger relative to the implant during the charging sessions. Such coupling changes can be compensated for using the disclosed technique, with adjustments made in situ to ensure the fastest charging within safe temperature limits.

Figure 12:
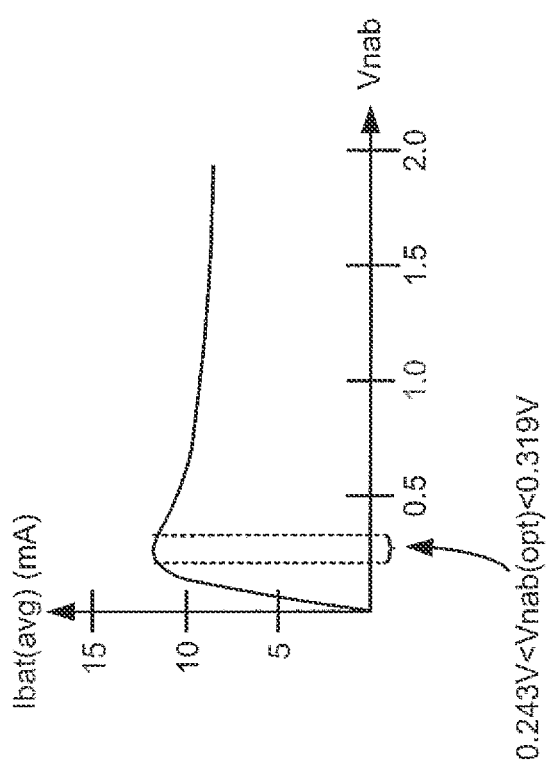
FIG. 12 illustrates application of the disclosed technique assuming definition of an optimal range for Vnab(opt).

To this point in the disclosure, it has been assumed that there is a single optimal Vnab value, Vnab(opt). However, Vnab(opt) can also represent a range of acceptable Vnab values. For example, the simulation 200 in FIG. 5C shows three values for Ibat(avg) over 11 mA (rows four through six), which correspond to Vnab values (FIG. 5A) of 0.243 to 0.319V. Assuming that operation at any of these battery charging currents provides satisfactorily quick charging of the implant battery 145, Vnab(opt) can be set to a range between 0.243 to 0.319V, as illustrated in FIG. 12. Therefore, if Vnab is reported within this range, the intensity at the external charger (Iprim) would not be changed. However, even if the intensity is not changed, it may still be prudent to vary the duty cycle in accordance with Vnab to ensure compliance with the heat limit. In this regard, notice in FIG. 5C that although Ibat(avg) does not change appreciably across the specified Vnab range (from 11.6 to 11.0 mA), the duty cycle changes rather sharply (from 82.9 to 53.6%). However, depending on the particulars of the simulation, and the conservative nature of the heat limit chosen, changing duty cycling within the Vnab(opt) range might not be necessary. In any event, defining Vnab(opt) as a range will simplify operation of the technique, and will require less frequent modification of the magnetic charging field at the external charger 151.

It should be understood that various parameters (e.g., Vnab (opt); a DC corresponding to a particular Vnab) can be interpolated or extrapolated from the simulation 200, and are therefore not necessarily constrained to actual values appearing in the simulation. However, such interpolation was not shown to keep discussion of the technique simple.

Many of the parameters determined herein (e.g., Vnab (opt)) result from the simulation 200, which simulation provides a convenient expedient for understanding the external charger/implant system. However, not all implementations of the technique will require the use of a simulation. Instead, empirical data, experimental models, direct analytical tools, or values chosen by other means, could be used depending upon consideration of factors deemed important by the designer.

The disclosed technique limits the total power dissipated by the implant. However, the technique can be constrained to control heating at only a portion of the implant. For example, in larger implants or implants with low heat conductivity, the technique can be employed to limit the local heating at any section of the implant. In such an application, the technique can use a parameter (perhaps different from Vnab) indicative of heating to that section, and limiting heating of that particular section to tolerable limits. Thus, this modification to the technique would only consider power dissipated as heat in the relevant section of the device.

Vnab is used in this disclosure as the measure indicative of excess power dissipation. However, other parameters from the implant indicative of incoming power and which can be used to control that power can also be used, such total power delivered to the battery, ripple of the coil voltage, ripple of the rectified voltage, on time of the rectifying circuit, duty cycle of the rectifying circuit, etc. Of course, these parameters could be measured or inferred in the implant in different ways.

Even though the technique describes the periodic measurement of parameters in the implant during a charging session, and periodic adjustment of the magnetic charging field, "periodic" should not be understood as necessarily taking such actions at set intervals. Instead, "periodic" should be understood as taking a plurality of such actions over time, even if not at set intervals.

While the inventions disclosed have been described by means of specific embodiments and applications thereof, numerous modifications and variations could be made thereto by those skilled in the art without departing from the literal and equivalent scope of the inventions set forth in the claims.

What is claimed is:

1. A method for charging a battery in an implantable medical device, comprising:
    generating a magnetic charging field using an external charger, the magnetic charging field for producing a battery charging current in the implantable medical device during a charging session;
    periodically measuring during the charging session a parameter in the implantable medical device;
    periodically telemetering during the charging session the parameter to the external charger; and
    periodically adjusting during the charging session in accordance with the parameter: (1) an intensity of the magnetic charging field to maximize an average battery charging current, and (2) a duty cycle of the magnetic charging field in accordance with a maximum power dissipation limit for the implantable medical device.

2. The method of claim 1, wherein the parameter is indicative of the produced battery charging current.

3. The method of claim 1, wherein the parameter comprises a voltage across charging circuitry serially coupled to the battery in the implantable medical device, wherein the battery charging current passes through the charging circuitry.

4. The method of claim 1, wherein adjusting the intensity comprises comparing the parameter to an optimal value in the external charger.

5. The method of claim 4, wherein the intensity is adjusted to bring the parameter to the optimal value.

6. The method of claim 1, wherein the external charger comprises a memory, wherein the memory comprises possible values for the parameter and a duty cycle associated with each value, wherein each duty cycle in the memory is determined in accordance with the maximum power dissipation limit for the implantable medical device.

7. The method of claim 6, wherein adjusting the duty cycle comprises retrieving a duty cycle from the memory using the parameter.

8. The method of claim 7, wherein the memory further comprises an optimal value for the parameter.

9. The method of claim 8, wherein the intensity is adjusted to bring the parameter to the optimal value.

10. The method of claim 1, wherein the parameter is telemetered to the external charger during off periods of the duty cycle.

11. A method for charging a battery in an implantable medical device, comprising:
    generating a magnetic charging field using an external charger, the magnetic charging field for producing a battery charging current in the implantable medical device;
    measuring a parameter in the implantable medical device;
    telemetering the parameter to the external charger; and
    adjusting an intensity and duty cycle of the magnetic charging field in response to the telemetered parameter,
    wherein adjusting the intensity comprises comparing the telemetered parameter to an optimal parameter stored in the external charger, and wherein adjusting the duty cycle comprises selecting a duty cycle stored in the external charger using the telemetered parameter.

12. The method of claim 11, wherein the parameter is telemetered to the external charger during an off cycle in the duty cycle of the magnetic charging field.

13. The method of claim 11, wherein the method repeats itself to iteratively adjust the intensity and duty cycle of the magnetic charging field.

14. The method of claim 11, wherein the parameter is indicative of heating in the implantable medical device during charging.

15. The method of claim 11, wherein adjusting the intensity and duty cycle additionally ensures that an average battery charging current is maximized without exceeding a power dissipation limit for the implantable medical device.

16. The method of claim 11, wherein the intensity is adjusted to bring the parameter to the optimal value.

* * * * *